(12) United States Patent
Nakamura

(10) Patent No.: US 6,649,630 B2
(45) Date of Patent: Nov. 18, 2003

(54) METHODS AND COMPOSITIONS CONTROLLING PESTS

(75) Inventor: Satoshi Nakamura, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/147,455

(22) Filed: May 17, 2002

(65) Prior Publication Data

US 2003/0013664 A1 Jan. 16, 2003

(30) Foreign Application Priority Data

May 21, 2001 (JP) .................................... 2001-150597

(51) Int. Cl.[7] ........................ A01N 43/40; A01N 31/335
(52) U.S. Cl. ........................ 514/327; 514/28; 514/450; 514/453; 536/7.1
(58) Field of Search ..................... 514/28, 327, 453; 536/7.1

(56) References Cited

U.S. PATENT DOCUMENTS

| | | | |
|---|---|---|---|
| 4,751,225 A | 6/1988 | Nishida et al. | 514/277 |
| 5,288,710 A | 2/1994 | Cvetovich | 514/30 |
| 5,439,924 A | 8/1995 | Miller | 514/345 |

*Primary Examiner*—Dwayne Jones

(74) *Attorney, Agent, or Firm*—Birch, Stewart, Kolasch & Birch, LLP

(57) ABSTRACT

The present invention provides compositions and methods which can provide a pesticidal effect. The compositions typically comprise 4-phenoxyphenyl 2-(2-pyridyloxy) propyl ether and an ether compound encompassed by formula I:

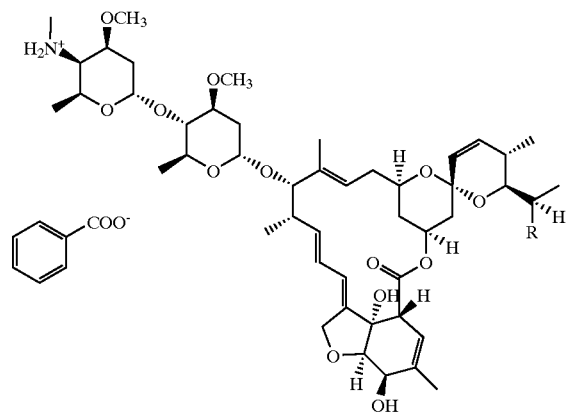

wherein R represents a methyl group or ethyl group.

The methods comprise applying a pesticidally effective amount of the composition to a pest of a habitat of a pest.

11 Claims, No Drawings

METHODS AND COMPOSITIONS CONTROLLING PESTS

TECHNICAL FIELD OF THE INVENTION

The present invention relates to compositions and methods, which can provide a pesticidal effect over pests.

BACKGROUND OF THE INVENTION

Various types of compositions have heretofore been developed and utilized in order to provide a pesticidal effect.

U.S. Pat. No. 4,751,225 describes 4-phenoxyphenyl 2-(2-pyridyloxy)propyl ether. The common name of 4-phenoxyphenyl 2-(2-pyridyloxy)propyl ether is pyriproxyfen.

U.S. Pat. No. 5,288,710 describes an ether compound encompassed by formula I:

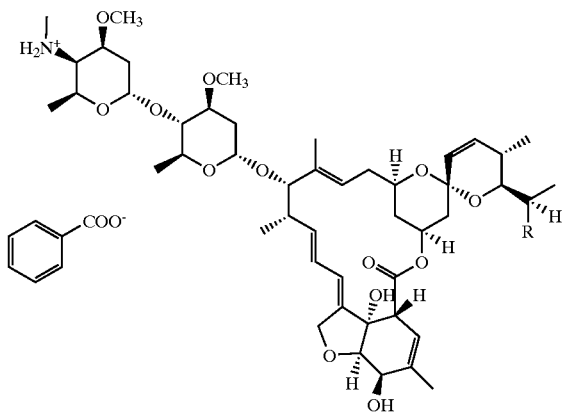

I wherein R represents a methyl group or an ethyl group.

SUMMARY OF THE INVENTION

The present invention provides compositions and methods. The composition comprises 4-phenoxyphenyl 2-(2-pyridyloxy)propyl ether and an ether compound encompassed by formula I:

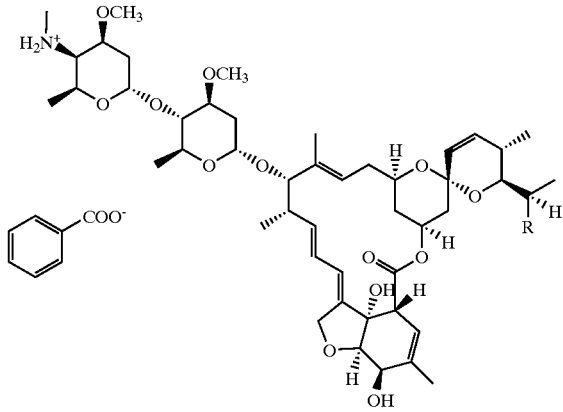

I wherein R represents a methyl group or ethyl group.

The method comprises applying a pesticidally effective amount of the composition to a pest or a habitat of the pest.

DETAILED DESCRIPTION OF THE INVENTION

The ether compounds encompassed by formula I and 4-phenoxyphenyl 2-(2-pyridyloxy)propyl ether are typically utilized as pesticidally active ingredients in the compositions of the present invention.

The compositions of the present invention may have present therein a mixture of the ether compounds encompassed by formula I. In such cases, the compositions may have a mixture of an ether compound encompassed by formula I, wherein in formula I, R represents an ethyl group with an ether compound encompassed by formula I, wherein in formula I, R represents a methyl group. The mixture thereof wherein the ether compound encompassed by formula I, wherein in formula I, R represents an ethyl group is approximately 90% by weight is known as an emamectin benzoate, wherein said weight percentage is based on the total weight of the provided mixture thereof. As the mixture thereof, the emamectin benzoate can be utilized in the compositions.

In the compositions, the ether compounds encompassed by formula I and 4-phenoxyphenyl 2-(2-pyridyloxy)propyl ether are typically present therein at an amount of 0.01 to 90% by weight and preferably 0.1 to 80% by weight, wherein said weight percentages are based on the total weight of the provided composition.

The typical weight to weight ratio of the ether compounds encompassed by formula I to 4-phenoxyphenyl 2-(2-pyridyloxy)propyl ether is to have for 1 part by weight of the ether compounds encompassed by formula I, 1 to 200 parts by weight of 4-phenoxyphenyl 2-(2-pyridyloxy)propyl ether, and preferably 10 to 100 parts by weight of 4-phenoxyphenyl ether, based on the total weight of the ether compounds encompassed by formula I and 4-phenoxyphenyl 2-(2-pyridyloxy)propyl ether in the compositions.

Such weight to weight ratios and amounts of the ether compounds encompassed by formula I and 4-phenoxyphenyl 2-(2-pyridyloxy)propyl ether can provide a pesticidally synergistic effect over the pest, when applied to a pest or a habitat of a pest.

The compositions can possess various forms in which the ether compounds encompassed by formula I and 4-phenoxyphenyl 2-(2-pyridyloxy)propyl ether are utilized as is, or as a formulation, with examples of such formulations including liquid formulations such as an oily formulation, emulsifiable concentrate, flowable and aerosol; solid formulations such as wettable powder, resin formulation, granule, dust and poison bait; and the like.

The formulations of the present invention can be formulated by conventional methods by which an ether compound encompassed by formula I and 4-phenoxyphenyl 2-(2-pyridyloxy)propyl ether are supported, dissolved or dispersed in a carrier selected accordingly to the formulation form, such as a solid carrier and a liquid carrier.

Examples of the solid carrier include clays such as kaolin clay, diatomaceous earth, synthetic hydrated silicon oxide, bentonite, Fubasami clay and terra alba; talcs; inorganic minerals such as ceramic, sericite, quartz, sulfur, activated carbon, calcium carbonate and naturally-occurring hydrated silica; chemical fertilizers such as ammonium sulfate, ammonium phosphate, ammonium nitrate, urea and ammonium chloride; resins such as polyolefin resin (e.g., low density polyethylene, high density polyethylene and polypropylene) and urethane resins (e.g., polyurethane); and the like.

Examples of the liquid carriers include water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosene and gas oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Optionally, a formulation adjuvant may be added to the formulations of the present invention, such as a surfactant, adhesive agent, dispersant, thixotropy-conferring compounds, stabilizer, propellant, anti-foaming agent, rust preventive agent, antifreeze, plasticizer, dye, pigment and the like.

More specifically, examples of the surfactant include alkyl sulfate ester salts, alkylsulfonate salts, alkylarylsulfonate salts, alkylaryl ethers, polyoxyethylenated derivatives of alkylaryl ethers, polyethyleneglycol ethers, polyvalent alcohol esters, sugar alcohol derivatives and the like.

Examples of the adhesive agents and dispersants include casein; gelatin; saccharides such as starch, gum arabic, cellulose derivatives and alginic acid; lignin derivatives; bentonite; and synthetic water-soluble polymers such as polyvinyl alcohol, polyvinylpyrrolidone and polyacrylic acids.

Examples of the thixotropy-conferring compounds include bentonite, aluminum magnesium silicate, xanthan gum, polyacrylic acid and the like.

Examples of the stabilizers include PAP (isopropyl acid phosphate), BHT (2,6-di-tert-butyl-4-methylphenol), BHA (2-tert-butyl-4-methoxyphenol and 3-tert-butyl-4-methoxyphenol), fatty acids such as stearic acid, fatty acid esters, vegetable oils such as soybean oil and cotton seed oil, mineral oils such as naphthalene, kerosene and diesel oil, and the like.

Examples of the propellants include carbon fluorocarbon gas, butane gas, LPG (liquefied petroleum gas), dimethyl ether, carbon dioxide and the like.

Examples of the anti-foaming agent include silicon resin mixtures such as ANTIFOAM C (manufactured by Dow Corning Corporation) and TSA730 (manufactured by GE Toshiba Silicones Company Limited), and the like.

As an example of the rust preventive agents, there is mentioned sodium benzoate.

Examples of the antifreeze include glycols such as ethylene glycol and polyethylene glycol, and the like.

Examples of the plasticizers include phthalate esters, stearic acids and the like.

Examples of the dyes or pigments include azo dyes such as disazo yellow and first yellow, and the like.

When utilized, the formulation adjuvant may be present in the formulations in an amount of from 0.001 to 50% by weight, and preferable from 0.01% to 30% by weight, wherein said weight percentages are based on the total weight of the provided composition.

The aerosol can be obtained by conventional methods, such as by packing the propellant and an oily formulation, emulsifiable concentrate or flowable comprising an ether compound encompassed by formula I and 4-phenoxyphenyl 2-(2-pyridyloxy)propyl ether, into an aerosol container having a propelling device, such as a spray can.

The poison bait of the present invention can be obtained by methods in which the ether compounds encompassed by formula I and 4-phenoxyphenyl 2-(2-pyridyloxy)propyl ether are mixed with the bait ingredients and other ingredients. Examples of the bait ingredients utilized to obtain the poison bait include grain powders, vegetable oils, saccharides, crystalline cellulose and the like. Examples of the other ingredients that may be utilized to obtain the poison bait include anti-oxidants such as dibutylhydrozytoluene and nordihydroguaiaretic acid; preservatives such as dihydroacetic acid; substances for preventing erroneous eating from children and pets such as red pepper powder; pest attractants such as cheese flavor, onion flavor, leek flavor, peanut oil and pheromones; and the like.

The compositions of the present invention are typically applied to the habitat of the pest, by applying the solid or liquid formulation to foliage of a plant or soil in the vicinity thereof. For example, there are mentioned methods in which dilutions of the wettable powder, emulsifiable concentrate or flowable is dispersed or sprinkled onto the foliage of the plant or onto the soil near where the plant is growing, methods in which the oily formulation or the oily formulation diluted with an organic solvent is dispersed or sprinkled onto the foliage of the plant or onto the soil near where the plant is growing, methods in which the aerosol is dispersed onto the foliage of the plant or onto the soil near where the plant is growing, methods in which the dusts are dispersed onto the foliage of the plant or onto the soil near where the plant is growing, methods in which the granules or poison baits are dispersed onto the soil near where the plant is growing, and the like.

Examples of the organic solvent utilized in the case to dilute the oily formulation, include mineral oils such as naphthalene, kerosene and diesel oil; vegetable oil such as soybean oil and cottonseed oil; and the like.

The compositions of the present invention are applied such that typically 10 to 10,000 g of the ether compounds encompassed by formula I and 4-phenoxyphenyl 2-(2-pyridyloxy)propyl ether are applied to every 1 hectare (10,000 m$^2$), and preferably such that 100 g to 1,000 g of the ether compounds encompassed by formula I and 4-phenoxyphenyl 2-(2-pyridyloxy)propyl ether are applied to every 1 hectare (10,000 m$^2$).

When diluting the emulsifiable concentrate, wettable powder or the flowable with water, the combined concentration of the ether compounds encompassed by formula I and 4-phenoxyphenyl 2-(2-pyridyloxy)propyl ether in the dilution is about 2 ppm to 500,000 ppm, and preferably 10 ppm to 100,000 ppm.

The resin formulations can be obtained by kneading the ether compounds encompassed by formula I and 4-phenoxyphenyl 2-(2-pyridyloxy)propyl ether into a resin with a conventional kneader and forming the mixture by injection, extrusion or compression molding. Alternatively, the resin formulations can be also obtained by impregnation, coating, printing the ether compounds encompassed by formula I and 4-phenoxyphenyl 2-(2-pyridyloxy)propyl ether on the resin, such that the ether compounds encompassed by formula I and 4-phenoxyphenyl 2-(2-pyridyloxy) propyl ether are supported on the resin. Such resin formulations can be applied to a habitat of a pest by placing the resin formulation to the vicinity of the plant, such as a crop.

Examples of the pest controlled by the compositions of the present invention include Hemipteran pests, Lepidopteran pests, Dipteran pests, Thysanopteran pests, Acarina pests and the like.

Examples of Hemipteran pests include Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leafhoppers) such as *Nephotettix cincticeps* and *Nephotettix virescens*; Aphididae (aphids) such as *Aphis gossypii* (cotton aphids), *Myzus persicae* (green peach aphid), *Aphis citricola, Lipaphis pseudobrassicae* (turnip aphid), *Nippolachnus piri*, *Toxoptera aurantii* (black citrus apid) and *Toxoptera ciidius* (brown citrus apid); stink bugs such as *Nezara antennata* (green stink bug), *Cletus punctiger*, *Riptortus clavetus* (bean bug) and *Plautia stali* (oriental stink bug); Aleyrodidae (whiteflies) such as *Trialeurodes vaporariorum* (greenhouse whitefly), *Bemisia tabaci* (sweetpotato whitefly) and *Bemisia argentifolli* (silverleaf whitefly); scales such as *Aonidiella aurantii* (California red scale), *Comstockaspis perniciosa* (San Jose scale), *Unaspis citri* (citrus snow scale), *Pseudaulacaspis pentagona* (white peach scale), *Saissetia oleae* (brown olive scale), *Lepidosaphes beckii* (purple scale), *Ceroplastes rubens* (red wax scale) and *Icerya purchasi* (cottonycushion scale); Tingidae (lace bugs); Psyllidae (suckers) and the like.

Examples of Lepidopteran pests include Pyralidae such as *Chilo suppressalis* (rice stem borer), *Cnaphalocrocis medinalis* (rice leafroller), *Ostrinia nubilalis* (European cornborer), *Parapediasia teterrella* (bluegrass webworm), *Notarcha derogata* (cotton leafroller) and *Plodia interpunctella* (Indian meal moth); Noctuidae such as *Spodoptera litura* (tobacco cutworm), *Pseudaletia separata* (rice armyworm), *Mamestra brassicae* (cabbage armyworm), *Agrotis ipsilon* (black cutworm), Trichoplusia spp., Heliothis spp. and Helicoverpa spp.; Pieridae such as *Pieris rapae*; Tortricidae such as Adoxophyes spp., *Grapholita molesta* (oriental fruit moth) and *Cydia pomonella*; Carposinidae such as *Carposina niponensis* (peach fruit moth); Lyonetiidae such as Lyonetia spp.; Lymantriidae such as Lymantria spp. and Euproctis spp.; Yponameutidae such as *Plutella xylostella*; Gelechiidae such as *Pectinophora gossypiella* (pink bollworm); Arctiidae (tiger moths) such as *Hyphantria cunea* (fall webworm); Tineidae such as *Tinea translucens* (casemaking clothes moth) and *Tineola bisselliella* (webbing clothes moth) and Yponanmeutidae (yponomeutid moth) such as *Plutella xylostella* (diamondback moth)); and the like.

Examples of Dipteran pests include Agromyzidae (leafminer flies) such as *Liriomyza trifolli*), *Delia platura* (seedcorn maggot), *Delia antiqua* (onion maggot), Tephritidae (fruit flies) and Drosophilidae (vinegar flies); and the like.

Examples of Thysanopteran pests such as *Thrips palmi*, *Thrips tabaci*, *Thrips hawaiiensis* (flower thrips), *Scirtothrips dorsalis* (yellow tea thrips), *Frankliniella intonsa* (flower thrips), *Frankliniella occidentalis* (western flower thrips) and *Ponticulothrips diospyrosi*;

Examples of Acarina pests include Tetranychidae (spider mites) such as *Tetranychus urticae* (two-spotted spider mite), *Tetranychus kanzawai* (Kanzawa spider mite), *Panonychus citri* (citrus red mite), *Panonychus ulmi* (European red mite) and Oligonychus spp.; Eriophyidae such as *Aculops pelekassi* (pink citrus rust mite) and *Calacarus carinatus* (purple tea mite); Tarsonemidae such as *Polyphagotarsonemus latus*), Tenuipalpidae (false spider mites) and Tuckerellidae; and the like.

The compositions may also utilize therein other insecticides, nematocides, acaricides, fungicides, herbicides, plant growth regulators, synergists, fertilizers, soil improving agents or animal foods.

Examples of such insecticides and acaricides include pyrethroid compounds such as permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin and 1-ethynyl-2-fluoro-2-pentenyl 3-(2,2-dichlorovinyl)-2,2-dimethylcyclopropanecarboxylate; organophosphorus compounds such as cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, calvinphos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, metoxadiazone and fenothiocarb; nereistoxin derivatives such as cartap, bensultap and thiocyclam; formamidine derivatives such as amitraz and chlordimeform; phenylpyrazole derivatives such as ethiprole; benzoylphenylurea compounds such as diflubenzuron, teflubenzuron, chlorfluazuron, flufenoxuron, triflumuron, hexaflumuron, lufenuron and novaluron; triazine derivatives such as cyromazine; thiadiazine derivatives such as buprofezine; juvenoid compounds such as methoprene, hydroprene, fenoxycarb and diofenolan; halofenozide; chromafenozide; chlorofenapir; phenisobromolate; quinomethionate; propargit; fenbutatin oxide; hexythiazox; clofentezine; fenpyroximate; tebufenpyrad; pyrimidifen; polynactin complex; milbemectin; azadirachtin; and the like.

EXAMPLES

Next, the present invention is described in more detail with the formulation examples and the test examples, but the present invention is not limited thereto.

Further, unless indicated otherwise, "parts" refers to "parts by weight".

Formulation Example 1

A part of the ether compound encompassed by formula I, 10 parts of 4-phenoxyphenyl 2-(2-pyridyloxy)propyl ether, 8 parts of polyoxyethylene alkylaryl ether, 2 parts of sodium alkylarylsulfonate and 79 parts of xylene are mixed to obtain a emulsifiable concentrate.

Formulation Example 2

A part of an ether compound encompassed by formula I, 10 parts of 4-phenoxyphenyl 2-(2-pyridyloxy)propyl ether, 3 parts by sodium alkylbenzenesulfonate, 3 parts of sodium ligninsulfonate and diatomaceous earth is uniformly mix pulverized with a jet air mill to obtain a wettable powder.

Formulation Example 3

Five-tenths (0.5) parts of an ether compound encompassed by formula I, a parts of 4-phenoxyphenyl 2-(2-pyridyloxy)propyl ether, 48.5 parts of talc and 50 parts of clay are uniformly mix pulverized to obtain a dust.

Formulation Example 4

After uniformly dissolving 5 parts of polyoxyethylenestyrylphenyl ether sulfate, 20 parts of a 1% aqueous xanthan gum and 3 parts of a smectite mineral in 60 parts of water as well as adding thereto 2 parts of an ether compound encompassed by formula I and 10 parts of 4-phenoxyphenyl 2-(2-pyridyloxy)propyl ether, the resulting mixture is wet pulverized with a sand mill to obtain a flowable.

Formulation Example 5

A tenth (0.1) part of an ether compound encompassed by formula I and 0.2 parts of 4-phenoxyphenyl 2-(2-pyridyloxy)propyl ether are dissolved in 5 parts of trichloroethane, and mixed with 89.7 parts of deodorized kerosene to obtain an oily formulation.

Formulation Example 6

Two-hundreths (0.02) parts of an ether compound encompassed by formula I and 0.1 part of 4-phenoxyphenyl 2-(2-pyridyloxy)propyl ether is dissolved in 10 parts of acetone. After the resulting mixture is then uniformly mixed with 99.88 parts of animal pet food granules (Breeding Solid Food Powder CE-2: Japan Clea Company Limited), the acetone therein is air dried to obtain a poison bait.

Formulation Example 7

After a part of an ether compound encompassed by formula I and a part of 4-phenoxyphenyl 2-(2-pyridyloxy) propyl ether is mix knead into 98 parts of a polyethylene resin (Sumikathene: Sumitomo Chemical Company Limited), that was pelleted. The pellets are extruded at 160 to 180° C. with a inflation film device to obtain a film resin formulation.

Test Example: Pesticidal Test with *Plutella xylostella*

Dilutions 1 to 5 were produced by diluting with water, Formulation A and/or Formulation B. Formulation A was an emulsifiable concentrate comprising 1% w/v of emamectin benzoate as an active ingredient, which comprises the mixture of the ether compound encompassed by formula I, wherein in formula I, R represents a methyl group and approximately 90% by weight of the ether compound encompassed by formula I, wherein in formula I, R represents an ethyl group (commercial name: Afirm, Syngenta Company). Formula B was an emulsifiable concentrate comprising 10% w/v of 4-phenoxyphenyl 2-(2-pyridyloxy) propyl ether as an active ingredient (commercial name: Lano, Sumitomo Chemical Company Limited).

Dilution 1 was produced by diluting Formulation A, so that emamectin benzoate was diluted to 1 ppm, as shown in Table 1.

Dilution 2 was produced by diluting Formulation B, so that 4-phenoxyphenyl 2-(2-pyridyloxy)propyl ether was diluted to 100 ppm, as shown in Table 1.

Dilution 3 was produced by diluting Formulation B, so that 4-phenoxyphenyl 2-(2-pyridyloxy)propyl ether was diluted to 50 ppm, as shown in Table 1.

Dilution 4 was produced by diluting a mixture of Formulation A and Formulation B, so that emamectin benzoate was diluted to 1 ppm and 4-phenoxyphenyl 2-(2-pyridyloxy) propyl ether was diluted to 100 ppm, as shown in Table 1.

Dilution 5 was produced by diluting a mixture of Formulation A and Formulation B, so that emamectin benzoate was diluted to 1 ppm and 4-phenoxyphenyl 2-(2-pyridyloxy) propyl ether was diluted to 50 ppm, as shown in Table 1.

After placing 6 potted cabbages in a green house infested with *Plutella xylostella* (diamondback moth) for 2 days, the number of larvae on the cabbages were analyzed. About identical amounts of a dilution of Formulation A, a dilution of Formulation B as well as a dilution of a mixture of Formulation A and Formulation B, as referred to in Table 1 below, were then sprayed, respectively, over 5 of the entire potted cabbages.

After spraying, the potted cabbages were then allowed to dry. Each of the sprayed cabbages and the untreated but larvae infested 6th cabbage were then placed in a 25° C. green house. Three (3) days thereafter, the number of living larvae on the cabbages were analyzed. The results are shown in Table 1.

TABLE 1

| | concentration of ingredients (ppm) | | living larvae per cabbage | | |
| --- | --- | --- | --- | --- | --- |
| | emamectin benzoate | 4-phenoxyphenyl 2-(2-pyridyloxy)propyl ether | before treatment | After treatment | mortality rate (%) |
| Dilution 1 | 1 | 0 | 24 | 23 | 4 |
| Dilution 2 | 0 | 100 | 29 | 12 | 59 |
| Dilution 3 | 0 | 50 | 33 | 21 | 36 |
| Dilution 4 | 1 | 100 | 23 | 0 | 100 |
| Dilution 5 | 1 | 50 | 36 | 0 | 100 |
| Untreated | 0 | 0 | 30 | 39 | |

The results above evidence that an excellent pesticidal effect can be achieved with the compositions of the present invention.

What is claimed is:

1. A composition comprising:
   a synergistic effective amount of 4-phenoxyphenyl 2-(2-pyridyloxy)propyl ether and an ether compound encompassed by formula I:

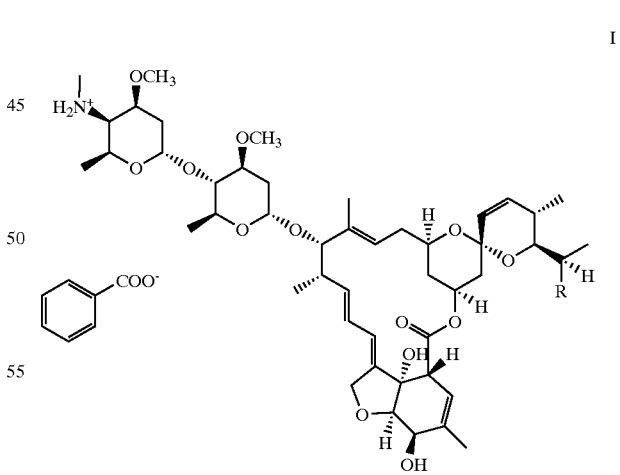

wherein R represents a methyl group or ethyl group.

2. The composition according to claim 1, wherein the ether compound is a mixture comprising:
   an ether compound encompassed by formula I, wherein in formula I, R represents an ethyl group and
   an ether compound encompassed by formula I, wherein in formula I, R represents a methyl group.

3. The composition according to claim 1, wherein the ether compound encompassed by formula I is emamectin benzoate.

4. A method comprising applying a pesticidally effective amount of the composition of claim 1 to a pest or a habitat of a pest.

5. The method according to claim 4, wherein the habitat of the pest is a plant or soil.

6. The composition according to claim 1, wherein the weight ratio of 4-phenoxyphenyl 2-(2-pyridyloxy)propyl ether and the ether compound encompassed by formula I is in the range of 1:1 to 1:200.

7. The composition according to claim 1, wherein the weight ratio of 4-phenoxyphenyl 2-(2-pyridyloxy)propyl ether and the ether compound encompassed by formula I is in the range of 1:10 to 1:100.

8. The composition according to claim 1, wherein the weight ratio of 4-phenoxyphenyl 2-(2-pyridyloxy)propyl ether and the ether compound encompassed by formula I is in the range of 1:50 to 1:100.

9. A method comprising applying a pesticidally effective amount of the composition of claim 6 to a pest or a habitat of a pest.

10. A method comprising applying a pesticidally effective amount of the composition of claim 7 to a pest or a habitat of a pest.

11. A method comprising applying a pesticidally effective amount of the composition of claim 8 to a pest or a habitat of a pest.

* * * * *